United States Patent [19]

DiPisa, Jr.

[11] Patent Number: 4,662,885
[45] Date of Patent: May 5, 1987

[54] PERCUTANEOUSLY DELIVERABLE INTRAVASCULAR FILTER PROSTHESIS

[75] Inventor: Joseph A. DiPisa, Jr., Flushing, N.Y.

[73] Assignee: Becton, Dickinson and Company, Franklin Lakes, N.J.

[21] Appl. No.: 772,218

[22] Filed: Sep. 3, 1985

[51] Int. Cl.$^4$ ............................................. A61F 2/04
[52] U.S. Cl. ...................................... 623/12; 623/1; 128/325; 128/334 R
[58] Field of Search ............. 128/334 R, 325; 604/11, 604/14; 623/1, 11, 12

[56] References Cited

U.S. PATENT DOCUMENTS

| | | | |
|---|---|---|---|
| 3,049,125 | 8/1962 | Kriwkowitsch | 128/325 |
| 3,050,066 | 8/1962 | Koehn | 128/325 |
| 3,435,824 | 4/1969 | Gamponia | 128/334 R |
| 3,516,408 | 6/1970 | Montanti | 128/334 R |
| 3,688,318 | 9/1972 | Alfano | 128/334 R X |
| 3,952,747 | 4/1976 | Kimmell, Jr. | 128/325 X |
| 3,991,767 | 11/1976 | Miller, Jr. et al. | 128/334 X |
| 4,140,126 | 2/1979 | Choudhury | 128/325 |
| 4,183,102 | 1/1980 | Guiset | 623/66 X |
| 4,230,119 | 10/1980 | Blum | 128/334 R X |
| 4,425,908 | 1/1984 | Simon | 128/325 X |
| 4,441,495 | 4/1984 | Hicswa | 128/325 |
| 4,539,716 | 9/1985 | Bell | 623/1 |

FOREIGN PATENT DOCUMENTS 0764684 9/1980 U.S.S.R. ............................ 128/325

Primary Examiner—Richard J. Apley
Assistant Examiner—Alan W. Cannon
Attorney, Agent, or Firm—Richard J. Rodrick

[57] ABSTRACT

An intravascular prosthesis comprises a lining rolled upon itself around an axis so that it is introducible into a vascular lumen. An inflatable channel is included for unrolling the lining when the prosthesis is positioned within the lumen so that the lining may engage the vascular wall to provide support therefor. A filter is provided for filtering the blood which passes through the prosthesis when the lining is unrolled.

15 Claims, 17 Drawing Figures

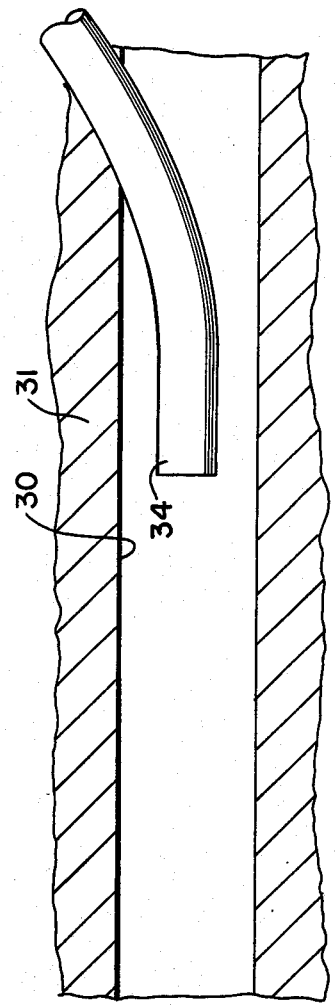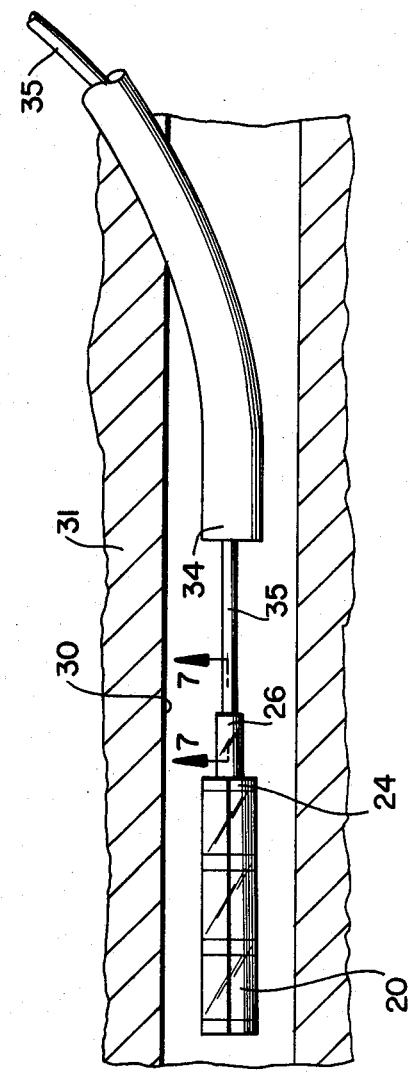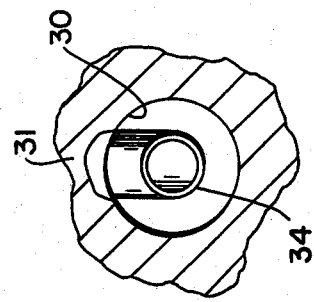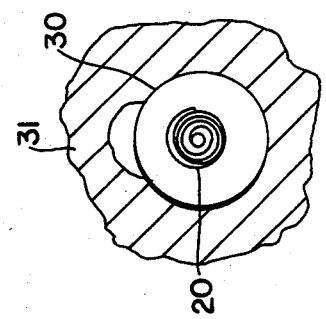

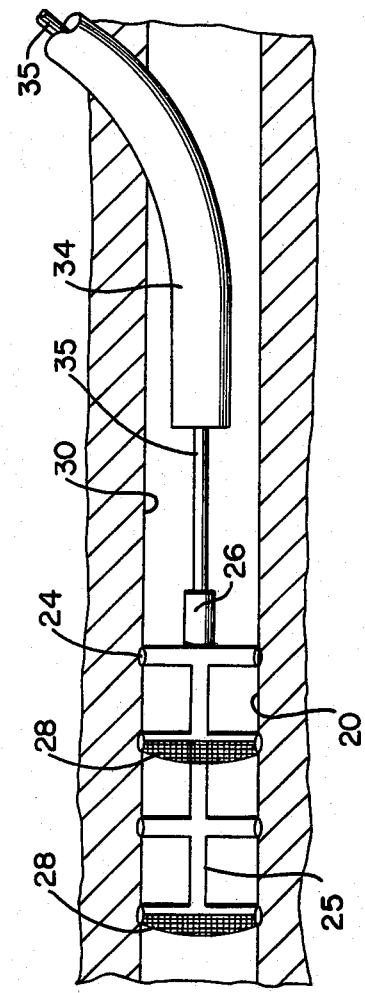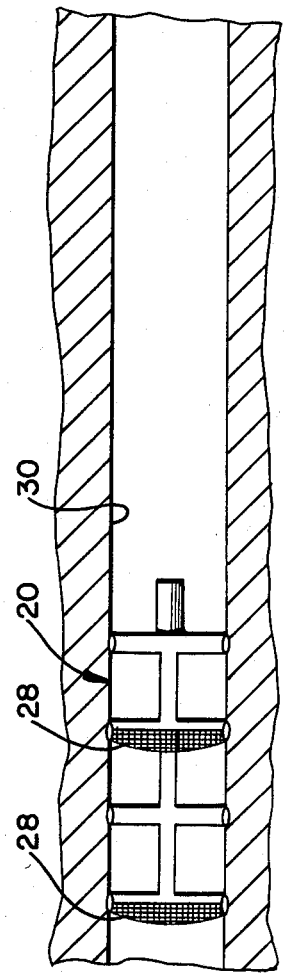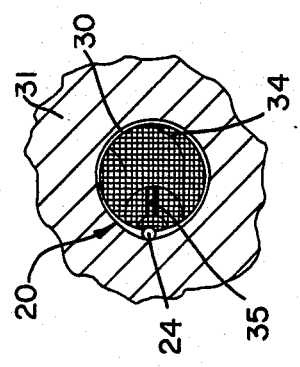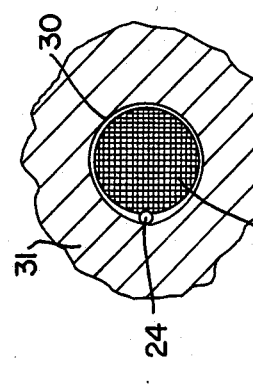
Fig. 10
Fig. 11
Fig. 12
Fig. 13

PERCUTANEOUSLY DELIVERABLE INTRAVASCULAR FILTER PROSTHESIS

BACKGROUND OF THE INVENTION

1. Field of the Invention

The present invention relates to an intravascular prosthesis, and more particularly, concerns a percutaneously deliverable prosthesis suitable for the intravascular filtration of blood so that migration of blood clot emboli may be prevented.

2. Description of the Prior Art

Blood vessels of humans or animals undergo a natural degenerative process or are sometimes subject to weakness. In weakened blood vessels, aneurysms may occur. The degenerative effect on blood vessels may also cause a narrowing or constriction of the lumen of the vessel so that blood flow is restricted. In other degenerative situations, or for other reasons, clots or emboli may occur which, should they migrate within the intravascular system, could be very dangerous.

With respect to the aforementioned intravascular problems, surgical intervention has been the primary technique for providing relief. For example, aneurysm repair involves a surgical procedure in which an intraluminal vascular prosthesis is inserted into the damaged vessel to reconstruct the section that needs repair. For clogged blood vessels, the excision of thickened atheromatous areas of the vessel has been performed by an endarterectomy procedure. Vascular filter, such as those placed in the vena cava, presently involves the positioning of a expandable structure or balloon within the vena cava. Such filters have been known to migrate, and are often difficult to properly orient within the vena cava. These and other intravascular therapy procedures of an invasive nature are not only risky, but are also costly.

Angioplasty procedures, using expandable balloons, have been developed for widening the lumen of diseased, constricted blood vessels. Many of these angioplasty procedures are performed percutaneously so that the balloon is introduced into the blood vessel through a catheter inserted through the skin into the vascular system. After the inflation of the expandable balloon widens the clogged blood vessel, it is withdrawn from the blood vessel through the introducer catheter. Balloon catheters are also available in which the inflated balloon is detachable from the catheter once inflated within the blood vessel. The inflated, detached balloon occludes the blood vessel, and is therefore useful in such procedures as varicocele treatment. Such a detachable balloon catheter system, known as the MINIBALLOON TM catheter, is sold by Becton, Dickinson and Company, Paramus, N.J.

Although inflatable and detachable balloon catheter procedures, performed percutaneously, are known and available for some intravascular therapy applications, surgery is still relied upon for other applications. Less invasive techniques are being sought for blood vessel repair, reconstruction and filtering, as well as vessel occlusion, blood flow regulation or flow assist. The present invention is directed to a device which provides for minimal invasive methods of intravascular therapy. In particular, the present invention is directed to an intravascular prosthesis, percutaneously deliverable, which is suitable for the filtration of blood clot emboli in the blood and for the reinforcement or reconstruction of weakened blood vessels, as well as aneurysm repair.

Two copending patent applications, having a common assignee herewith, Ser. No. 772,216 and Ser. No. 772,217 both filed on Sept. 3, 1985 relate to those intravascular therapy applications involving blood vessel reinforcement without filtering, and to blood vessel occlusion and blood flow regulation.

SUMMARY OF THE INVENTION

The intravascular prosthesis of the present invention comprises a lining rolled upon itself around an axis so that it is introducible into a vascular lumen. Means, associated with the lining, are provided for unrolling the lining when the prosthesis is positioned within the lumen so that the lining may engage the vascular wall to provide support therefor. Filter means are included to filter the blood which passes through the prosthesis when the lining is unrolled.

In a preferred embodiment of this aspect of the invention, an inflatable channel is associated with the lining and is rolled upon itself around the same longitudinal axis around which the lining is rolled. The channel includes a filling port for the introduction of fluid into the channel for inflation. The lining and the channel have the capability of unrolling when the channel is inflated so that the lining may engage the vascular wall. A porous filter, such as a flexible, reticulated member, is connected to the lining. The filter is positioned so that, when the lining is unrolled, the filter extends substantially transversely across the interior of the unrolled lining. Blood clots, atheromatous debris or other emboli are thus prevented from passing through the prosthesis.

Another aspect of the present invention is an intravascular prosthesis assembly which includes a lining, means for unrolling and filter means, as described above, and activation means connected to the means for unrolling for causing the lining to unroll.

A further aspect of the present invention is an intravascular prosthesis kit comprising a prosthesis, as described above, and activation means for connection to the means for unrolling for causing the lining to unroll.

In accordance with the principles of the present invention, the intravascular prosthesis hereof has significant advantages over known devices for intravascular therapy, almost all of which require surgical intervention. The present prosthesis may be delivered to, positioned and detached in, or withdrawn from a blood vessel through a percutaneous catheter or cannula. As a result, the present prosthesis obviates costly and risky surgery, and allows for a quick, simple and least invasive method of vascular filtration. Placement of the prosthesis of the present invention may be performed under fluoroscopic visualization and, perhaps, under local anesthesia. In certain aspects of the present invention, the unrolling feature may be reversed so that the prosthesis may be removed from the blood vessel, or even replaced should such replacement be required. In other instances, the lining of the prosthesis may be seeded with cells, such as endothelial cells, or otherwise treated to enhance and facilitate the features of the invention and to prevent blood clots from forming. Since the prosthesis of the present invention may be designed to be detachable, it may be left in the blood vessel as a permanent implant. This prosthesis has specific application to vena cava filtering, but may also have other blood filtering applications, such as the prevention of intracranial emboli in those patients who experience transient ischemis attacks or are otherwise susceptible to stroke. It can be seen that the versatility of the present invention provides for many different intravascular therapy applications.

BRIEF DESCRIPTION OF THE DRAWINGS

FIG. 3 is a cross-sectional view of a blood vessel illustrating the positioning of the introducer catheter for the delivery of the intravascular prosthesis into the blood vessel;

FIG. 4 is an end view of the blood vessel illustrated in FIG. 3;

FIG. 5 is a cross-sectional view of the blood vessel illustrating the delivery of the intravascular prosthesis in its normal, rolled condition;

FIG. 6 is an end view of the blood vessel and intravascular prosthesis illustrated in FIG. 5;

FIG. 10 is a cross-sectional view of the blood vessel illustrating the intravascular prosthesis in the unrolled condition engaging the intravascular wall;

FIG. 11 is an end view of the blood vessel and intravascular prosthesis illustrated in FIG. 10;

FIG. 12 is a cross-sectional view of the blood vessel illustrating the intravascular prosthesis implanted in the blood vessel after the introducer catheter and the filling catheter have been removed; and FIG. 13 is an end view of the blood vessel and the intravascular prosthesis illustrated in FIG. 12.

DETAILED DESCRIPTION

Figure 1:
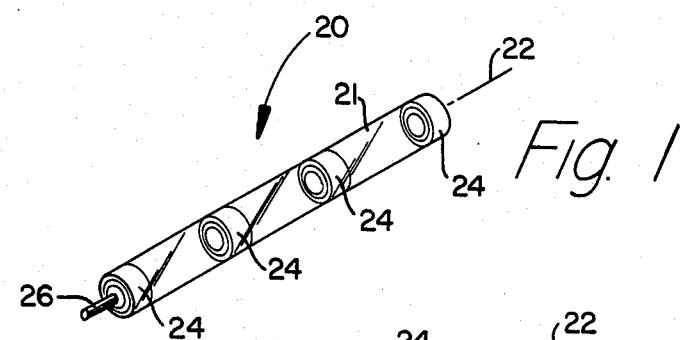
FIG. 1 is a perspective view of the preferred embodiment of the intravascular prosthesis of the present invention illustrated in its normal, rolled condition.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting now to the drawings, and FIG. 1 in particular, there is illustrated the preferred intravascular prosthesis 20 of the present invention as it appears in the normal, relaxed condition. Prosthesis 20 includes a segment of a lining material 21 which is preferably flexible in nature. Lining 21 is rilled upon itself around a longitudinal axis 22 so that a cylinder is formed. For purposes of the present invention, the term "rolled upon itself" regarding the lining not only includes rolling, but also covers folding, wrapping, gathering or the like of the lining so that the lining may be reduced in size and then subsequently expanded or opened-up to carry out the functions contemplated by the present invention. The number of turns or rolls of lining 21 is normally not important to the present invention, except that a relatively tightened or small diameter roll is more amenable to entering blood vessels having a small vascular lumen. The length of lining 21 may vary according to the intended purpose of the invention. It is also desirable that, once rolled, lining 21 remain in the rolled condition until the prosthesis has been positioned within the blood vessel.

Figure 2:
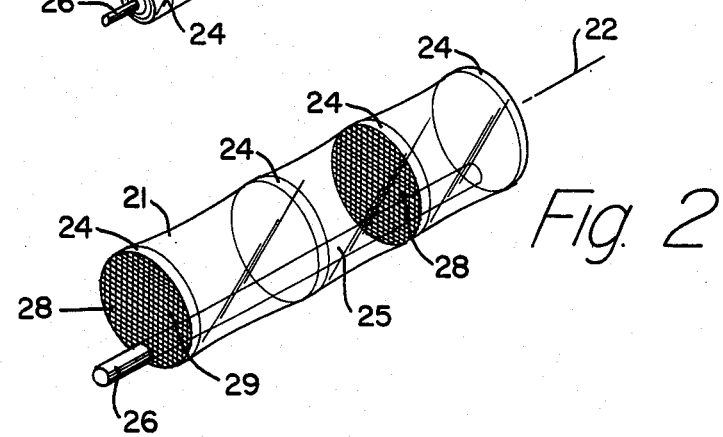
FIG. 2 is a perspective view of the preferred embodiment of the intravascular prosthesis illustrated in the unrolled, inflated condition as it may appear when engaged against the vascular wall.

Once positioned in the blood vessel as will be more completely described hereinafter, radial expansion of the prosthesis is to be achieved. Such expansion occurs by the unrolling of lining 21. To facilitate this unrolling, one or more inflation channels are provided to unroll lining 21. In FIG. 2, which illustrates prosthesis 20 in the unrolled condition, four such inflation channels 24 are provided. It is understood that the number of such inflation channels may vary according to many factors including the desired support to be provided by the prosthesis, the length of the prosthesis, the opening of the vascular lumen, etc. Each inflation channel 24 is preferably a tubular band of material circumferentially oriented around longitudinal axis 22 as well as around lining 21. Inflation channels 24 are preferably connected to lining 21 so that the axial spacing between each channel may be maintained and so that stability of the prosthesis may occur. Interconnecting inflation channels is a conduit 25 which is in fluid communication with each of the inflation channels. A filling port 26, also in fluid communication with inflation channels 24 and conduit 25, is provided so that fluid may be introduced to the interior of the inflation channels. The details of filling port 26 will be described more fully hereinafter.

In the normal, relaxed condition, inflation channels 24 are also rolled upon themselves around longitudinal axis 22 so that the rolled prosthesis appears as illustrated in FIG. 1. Upon the introduction of fluid into inflation channels 24, they expand causing their own unrolling as well as the unrolling of lining 21 so that, upon full inflation, prosthesis 20 appears as illustrated in FIG. 2. In the unrolled condition the inflation channels and lining define an open interior passageway 27 along longitudinal axis 22 so that blood may freely pass through the prosthesis. Although not necessary for every application of the present invention, there may be circumstances when the present invention is not intended for a permanent implant, or perhaps, the hemodynamics related to the prosthesis dictate that it be removed from the blood vessel. In such circumstances, it is preferred that inflation channels 24, as well as lining 21, have the capability of returning to the rolled condition after inflation of the channels. Having such a memory capability, whereby the unrolling of the prosthesis is reversed, permits the prosthesis to be removed or retrieved from the blood vessel should physiological conditions so warrant.

As seen in FIG. 2, prosthesis 20 includes two filters 28 spaced apart from each other along longitudinal axis 22. These filters are preferably flexible, open-mesh or reticulated screens having pores 29 therethrough so that blood may pass through the filters. However, the filters serve to catch blood clot emboli which may be present in the blood flow and prevent the migration of the emboli to other parts of the vascular system. A suitable pore rating is selected for the filters to achieve such emboli-catching function. The filters should also have sufficient flexibility so that they may be folded within the rolled prosthesis. Although two filters are herein described, it is understood that one such filter, or more than two, could be employed for the present invention. Each filter 28 may be connected to the lining or an inflatable channel by adhesives, thermoplastic welding or other compatible technique.

Insofar as the prosthesis of the present invention is intended for intravascular use, it is preferred that all materials for the prosthesis be biocompatible. Inflation channels 24, lining 21 and filter 28 may be formed of flexible, polymeric material such as silicone, polyurethane or the like. In order to protect against the formation of a thrombosis, it may be desirable, especially when used in smaller bore vessels, to treat or seed lining 21 with cells to increase duration of patency. For example, lining 21 may be seeded with human endothelial cells inasmuch as these cells line the walls of blood vessels. Further, prosthesis 20 may be treated with heparin, other anti-clotting agents, plasma surface modification or the like to prevent blood clots from forming in the blood after the prosthesis is positioned in the vascular lumen.

Turning now to FIGS. 3 and 4, a blood vessel 30 is schematically illustrated within the body 31 of an animal or human. The skin of the patient has been pierced, as well as blood vessel 30, and a hollow introducer catheter 34 has been percutaneously positioned within the lumen of the blood vessel. Introducer catheter 34 serves primarily as a guide to introduce the intravascular prosthesis to the affected site within the blood vessel.

Delivery and positioning of intravascular prosthesis 20, in the rolled condition, is illustrated in FIGS. 5 and 6. It can be seen that prosthesis 20 is connected, by virtue of its filling port 26, to a catheter 35. It is preferred that catheter 35 be flexible and hollow so that it may deliver fluid from outside of the patient's body to inflation channels 24 in the intravascular prosthesis. The end of flexible catheter 35 outside of the patient may be connected to a fluid source (not shown) so that fluid may be delivered, preferably, under pressure, to the prosthesis inside the blood vessel.

Figure 7:
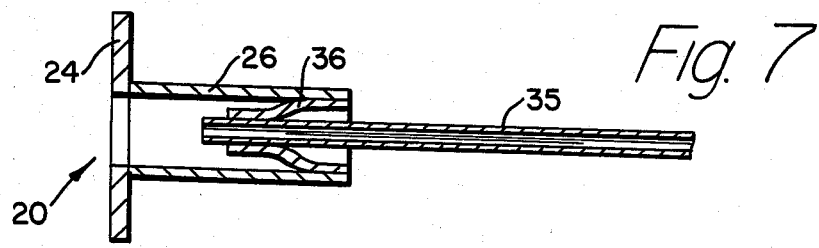
FIG. 7 is an enlarged cross-sectional view of the connection between the intravascular prosthesis and the catheter for providing fluid to the prosthesis.
Figure 8:
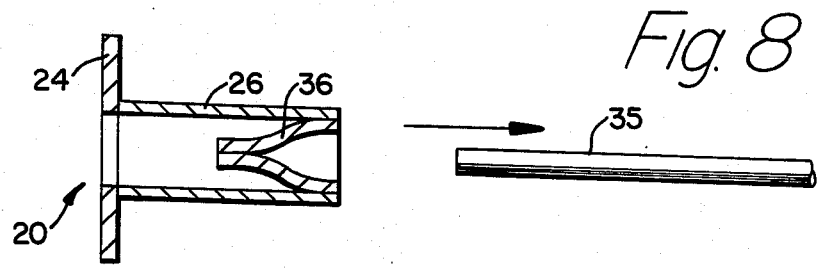
FIG. 8 is an enlarged cross-sectional view of the filling port of the prosthesis illustrating its fluid-tight closure after the filling catheter has been removed.

Reference is made to FIGS. 7 and 8 which illustrate the connection of catheter 35 to prosthesis 20, as well as the detachment of the prosthesis from the catheter. A valve 36 is included within filling port 26 of the prosthesis so that fluid may enter the inflation channels yet remain there without escaping after detachment of prosthesis 20 from tethering and filling catheter 35. In the embodiment illustrated in FIGS. 7 and 8, valve 36 is a duck-bill valve, although other embodiments of such a valve may be employed. Once prosthesis 20 has been unrolled due to the inflation pressure of the inflation channels, catheter 35 may be slipped out of filling port 26 and valve 36 whereby the valve closes and the fluid remains inside the prosthesis. The choice of fluids to inflate the inflation channels may include saline solution, an osmotic filling agent having an osomosis level to substantially balance the osmotic level of blood, or the fluid may include a hardening agent so that the prosthesis may be left as a permanent implant inside the blood vessel.

Figure 9A:
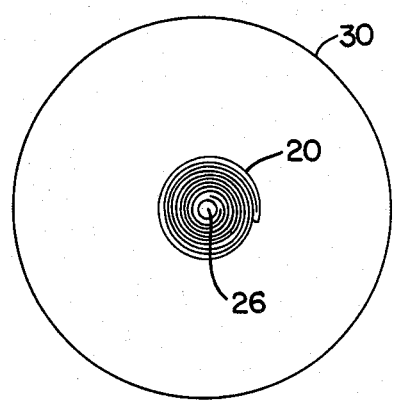
FIGS. 9a-9e are end views of the intravascular prosthesis inside the blood vessel illustrating the sequential unrolling of the prosthesis until it engages the vascular wall of the blood vessel.
Figure 9D:
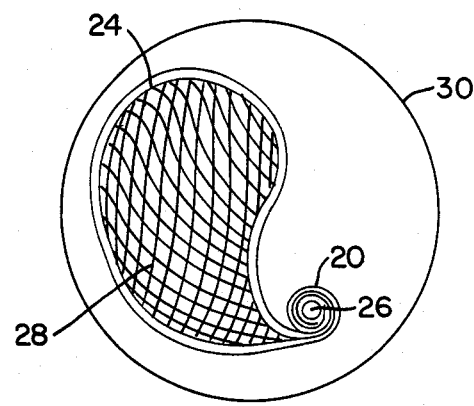
Figure 9B:
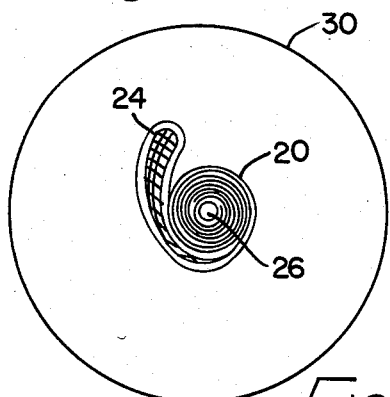
Figure 9E:
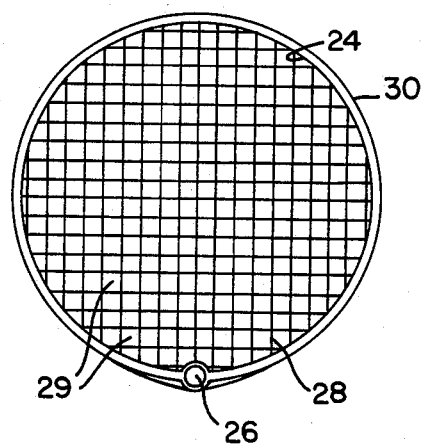
Figure 9C:
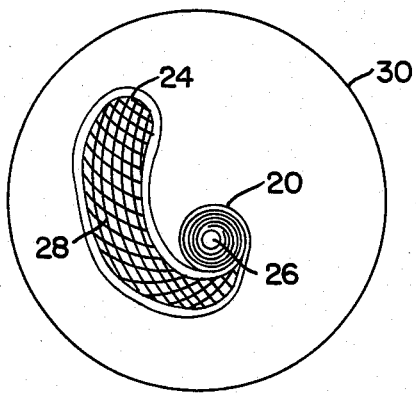

FIGS. 9a–9e graphically represent the sequential unrolling of intravascular prosthesis 20 inside blood vessel 30. In FIG. 9a, prosthesis 20 has been introduced into blood vessel 30 in the rolled condition. FIG. 9a is essentially an enlarged view of FIG. 6. As fluid is introduced into inflation channels 24, the fluid actuates an unrolling and expansion process, the intial stage of which is illustrated in FIG. 9b. FIGS. 9c and 9d represent further filling of inflation channels 24, with the inflation channels taking on a loop-like configuration. FIG. 9c further illustrates that filling port 26 has started to move toward the intravascular wall as the loop is being formed. The closeness of filling port 26 to the intravascular wall of blood vessel 30 is more clearly highlighted in FIG. 9d. Upon full inflation of inflation channels 24, the prosthesis engages the vascular wall as illustrated in FIG. 9e. Inasmuch as the prosthesis has been completely unrolled, interior passageway 27 is thereby formed along longitudinal axis 22 (as seen in FIG. 2) which permits blood to pass through the prosthesis. Filter 28 is also illustrated extending substantially transversely across the interior of the unrolled prosthesis so that it may prevent blood clots from passing through the prosthesis.

FIGS. 10 and 11 depict the unrolled prosthesis 20 engaging the wall of blood vessel 30. Catheter 35 which cooperates to activate the unrolling of the prosthesis by delivering fluid thereto is still connected to filling port 26. The expansion of prosthesis 20 due to inflation provides reinforcement and support of the blood vessel to which it is engaged. The radial expansion of the prosthesis produces a fixation effect within the blood vessel and permits filling catheter 35 to be withdrawn from filling port 26. The permanency of the fixation effect, as described above, is achieved by either or both of the following means: the valve in the filling port of the prosthesis serves to prevent the escape of fluid from the inflation channels of the prosthesis, or the prosthesis may be filled with a solidifying fluid as the final step before detachment of the catheter. If prosthesis 20 is merely for temporary purposes or because of physiological conditions should not remain within blood vessel 30, fluid inside the inflation channels may be withdrawn through filling catheter 35 whereupon prosthesis 20 reverts to its rolled condition. This reversibility feature will allow the removal or retrieval of prosthesis 20, if necessary or desired.

FIGS. 12 and 13, on the other hand, illustrate prosthesis 20 as a detached, permanent implant within blood vessel 30. Support and reinforcement are provided by the prosthesis which engages the vascular walls. Further, blood may freely flow through passageway 27 which is formed after the prosthesis has been unrolled, but blood clot emboli in the blood will be trapped by the mesh of filters 28.

Although it is preferred that filling catheter 35 be connected to filling port 26 of the prosthesis during initial assembly of the prosthesis, these components may be assembled just prior to use of the device. In this regard, a kit may be provided which includes the intravascular prosthesis, comprised of the lining, inflation channels and at least one filter, an introducer catheter and a filling catheter, along with other components which may facilitate the use of the device in a blood vessel.

Thus, the present invention provides a percutaneously deliverable intravascular prosthesis. The present invention is suitable for various intravascular therapy applications and is particularly useful for filtration of blood to prevent the migration of emboli. Such filtration may be achieved using the prosthesis of the present invention with minimal invasion of the patient's body thereby achieving a conservative approach for such medical procedures.

What is claimed is:

1. An intravascular prosthesis comprising:
    a lining rolled upon itself in a plurality of turns around a longitudinal axis so that it is introducible into a vascular lumen surrounded by a vascular wall;
    an inflatable channel associated with said lining and being rolled upon itself around said longitudinal axis, said channel including a filling port for the introduction of fluid into said channel for the inflation thereof, said lining and said channel having the capability of unrolling when said channel is inflated so that the lining may engage the vascular wall to provide support therefor; and
    a porous filter connected to said lining and positioned so that, when the lining is unrolled, said filter extends substantially transversely across the interior of said unrolled lining to prevent blood from passing through the prosthesis.

2. The prosthesis of claim 1 wherein the unrolled lining and channel, when the channel is inflated, defines an intravascular prosthesis having an open interior passageway along said longitudinal axis so that blood may pass therethrough, with said filter extending across said passageway to prevent blodo clots from passing therethrough.

3. The prosthesis of claim 1 wherein there is a plurality of rolled, inflatable channels associated with said lining and spaced axially from each other along said longitudinal axis.

4. The prosthesis of claim 3 wherein said inflatable channels are interconnected by a fluid conduit in fluid communication with said filling port so that all of said channels may be inflated.

5. The prosthesis of claim 1 wherein said filter is flexible.

6. The prosthesis of claim 5 wherein said filter is reticulated.

7. The prosthesis of claim 1 wherein there is a plurality of said filters spaced axially from each other along said longitudinal axis.

8. The prosthesis of claim 1 wherein said prosthesis is made of biocompatible material.

9. The prosthesis of claim 8 wherein said lining is seeded with endothelial cells.

10. The prosthesis of claim 8 wherein said prosthesis is treated to prevent blood clots from forming in the blood after said prosthesis is positioned in the vascular lumen.

11. The prosthesis of claim 1 wherein said lining and said channel have the capability of returning to the rolled condition after inflation of said channel.

12. The prosthesis of claim 1 which further includes a valve associated with said filling port so that fluid introduced into said channel is prevented from escaping thereby maintaining said channel in an inflated condition.

13. An intravascular prosthesis comprising:
    a lining rolled upon itself in a plurality of turns around an axis so that it is introducible into a vascular lumen surrounded by a vascular wall;
    means for unrolling the lining when the prosthesis is positioned within said lumen so that the lining may engage the vascular wall to provide support therefor, said means for unrolling further including actuation means for causing said lining to unroll, said actuation means being fluid introduced into said means for unrolling; and
    filter means for filtering the blood which passes through the prosthesis when said lining is unrolled.

14. An intravascular prosthesis assembly comprising:
    a lining rolled upon itself in a plurality of turns around an axis so that it is introducible into a vascular lumen surrounded by a vascular wall;
    means for unrolling the lining when the prosthesis is positioned within said lumen so that the lining may engage the vascular wall to provide support therefor, said means for unrolling including an inflatable channel;
    filter means for filtering the blood which passes through the prosthesis when said lining is unrolled; and
    activation means connected to said means for unrolling for causing said lining to unroll including an elongate portion extendable outside of the body in which said vascular lumen is located so that activation is achievable externally of said body, said elongate portion being a hollow catheter detachably connected to said channel so that fluid may be introduced through said catheter to said channel to inflate same.

15. The assembly of claim 14 wherein said channel includes a filling port into which said catheter is detachably connected, said filling port further including a one-way valve so that fluid introduced into said channel is prevented from escaping upon detachment of said catheter.

* * * * *